(12) United States Patent
Schulz et al.

(10) Patent No.: US 9,572,905 B2
(45) Date of Patent: Feb. 21, 2017

(54) STERILE INDICATOR FOR A STERILIZATION CONTAINER

(71) Applicant: Aesculap AG, Tuttlingen (DE)

(72) Inventors: Peter Schulz, Loeffingen (DE); Stefan Schuster, Villingen-Schwenningen (DE); Dieter Weisshaupt, Immendingen (DE)

(73) Assignee: Aesculap AG (DE)

( * ) Notice: Subject to any disclaimer, the term of this patent is extended or adjusted under 35 U.S.C. 154(b) by 357 days.

(21) Appl. No.: 14/254,204

(22) Filed: Apr. 16, 2014

(65) Prior Publication Data
US 2014/0312196 A1    Oct. 23, 2014

(30) Foreign Application Priority Data

Apr. 17, 2013    (DE) .................. 10 2013 103 889

(51) Int. Cl.
| *F16M 13/00* | (2006.01) |
| *A61L 2/28* | (2006.01) |
| *F16M 13/02* | (2006.01) |
| *A61L 2/04* | (2006.01) |

(52) U.S. Cl.
CPC .............. *A61L 2/28* (2013.01); *F16M 13/02* (2013.01); *A61L 2/04* (2013.01)

(58) Field of Classification Search
CPC .............. A61L 2/04; A61L 2/28; F16M 13/02
USPC ......................... 248/542; 116/221
See application file for complete search history.

(56) References Cited

U.S. PATENT DOCUMENTS

| 4,539,929 A | 9/1985 | Sestak et al. |
| 2003/0211618 A1* | 11/2003 | Patel ................. A61L 2/07 436/38 |
| 2005/0265889 A1* | 12/2005 | Wu .................. A61L 2/20 422/3 |

FOREIGN PATENT DOCUMENTS

| DE | 747432 | 9/1944 | |
| DE | 3316141 | 11/1984 | |
| DE | 3632674 A1 | 4/1988 | |
| DE | 202009010210 U1 | 10/2009 | |
| DE | 102009018817 | 10/2010 | |
| DE | EP 2305318 A1 * | 4/2011 | ............... A61L 2/26 |
| DE | 102011054827 A1 * | 5/2013 | ............... A61L 2/26 |
| EP | 0412571 | 2/1991 | |

OTHER PUBLICATIONS

German Search Report with partial translation issued in related German Application No. 10 2013 103 889.1, dated Feb. 25, 2014.

* cited by examiner

*Primary Examiner* — Gwendolyn Baxter
(74) *Attorney, Agent, or Firm* — RatnerPrestia

(57) ABSTRACT

A sterile display for a sterile container includes a thermally actuatable display apparatus for the display of a first and a second sterility condition of the sterile container. The display apparatus includes an adjustment mechanism having an actuator element which can be transferred, by external heating, from a first stress state in which the first sterility condition can be displayed, to a second stress state in which the second sterility condition can be displayed. The adjustment mechanism includes a thermo-bimetal element wherein, by its actuation, the actuator element of the adjustment mechanism can be transferred from the first stress state to the second stress state.

15 Claims, 4 Drawing Sheets

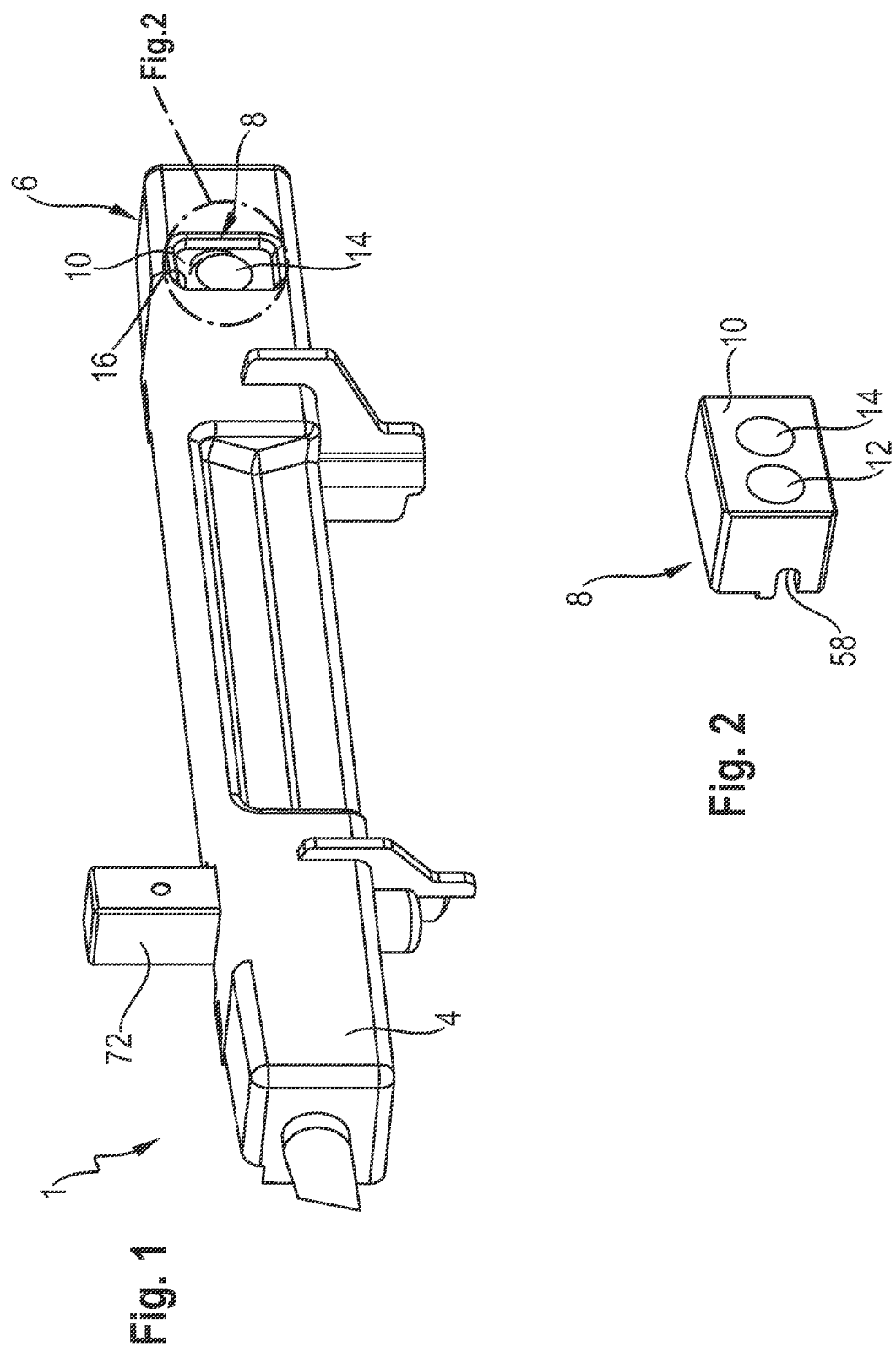

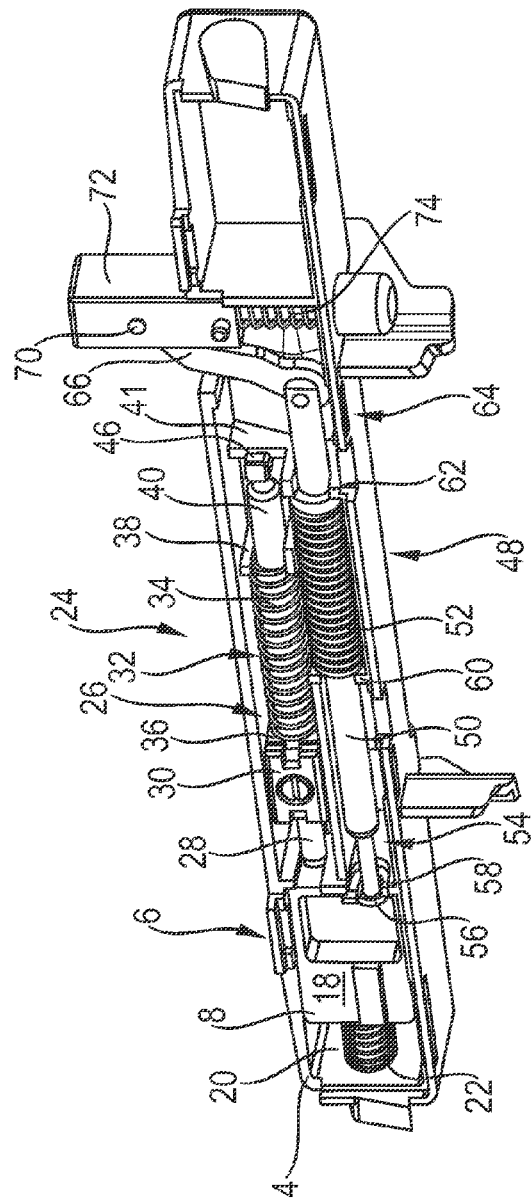
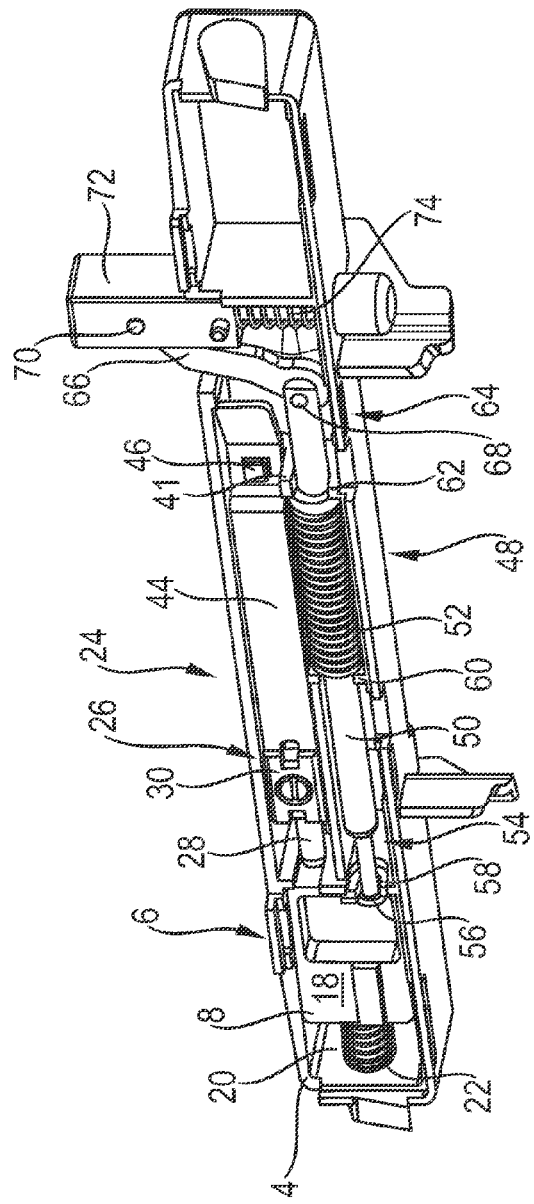

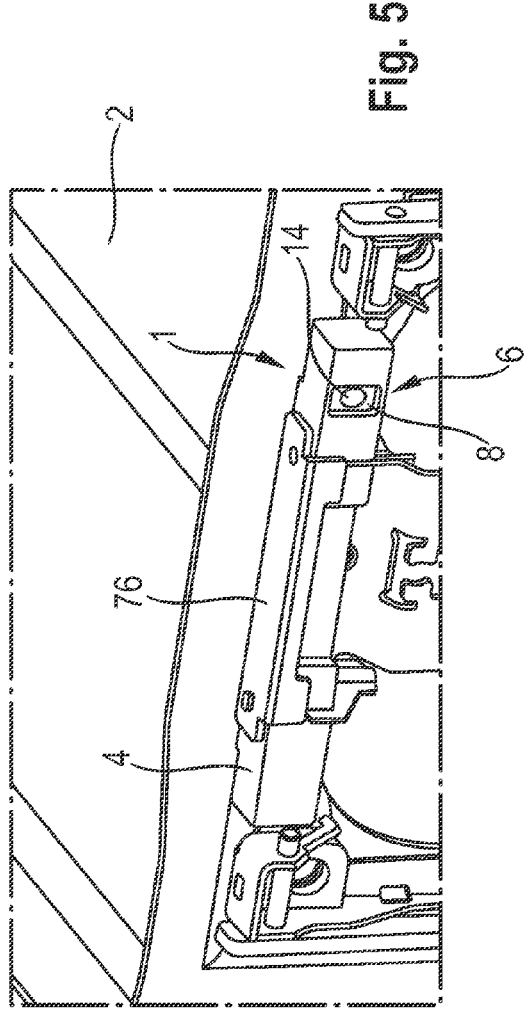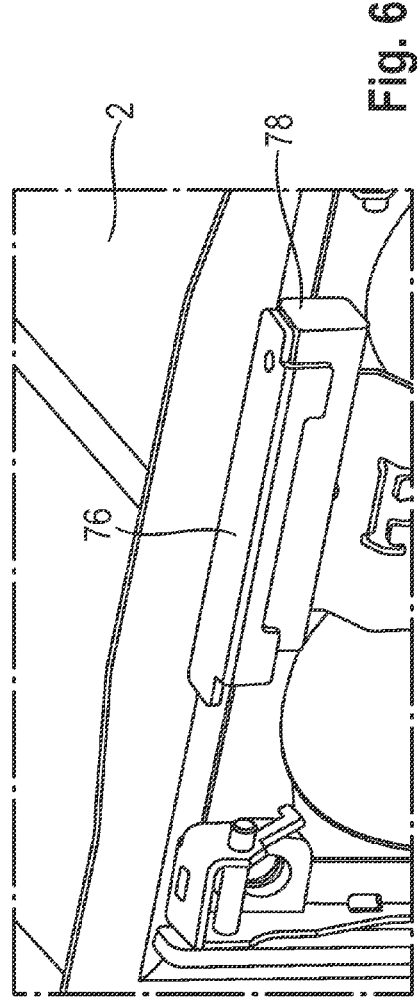

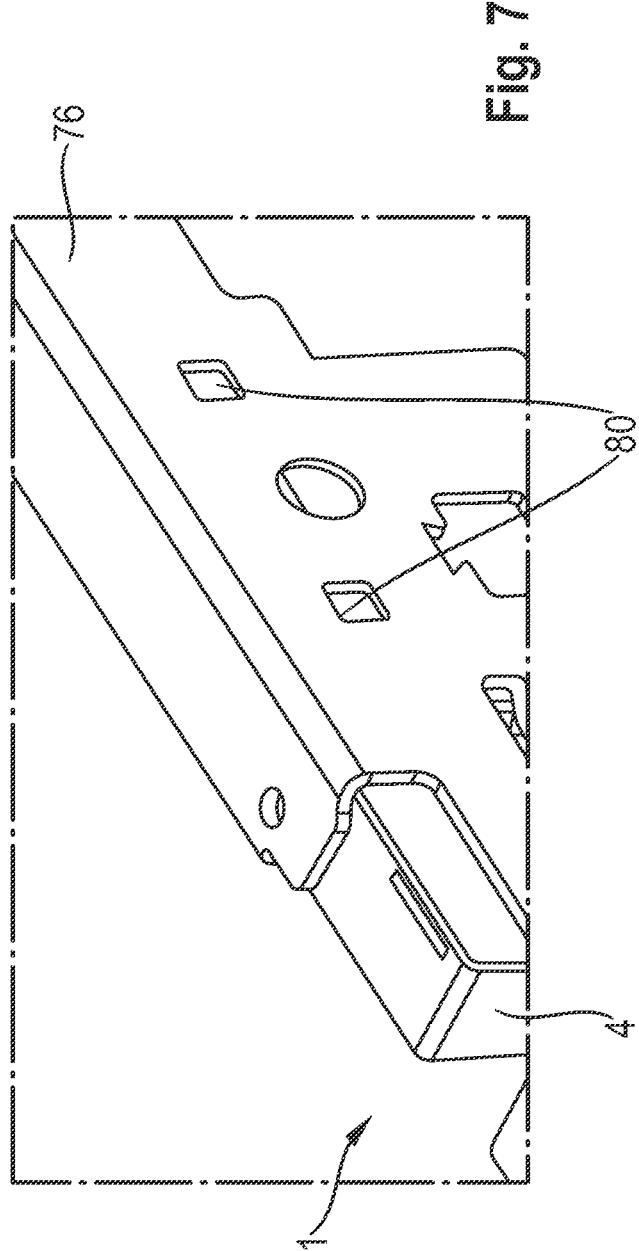

STERILE INDICATOR FOR A STERILIZATION CONTAINER

RELATED APPLICATIONS

This application claims the benefit of priority of German Application No. DE 10 2013 103 889.1, filed Apr. 17, 2013, the content of which is incorporated by reference herein in its entirety for all purposes.

FIELD

The invention relates to a sterile display or indicator for a sterile container.

BACKGROUND

It is known that in medicine or surgery, sterile containers are used which commonly can be loaded with surgical instruments designated for sterilization. During the sterilization process the instruments remain in the sterile container and are heated in it with a predetermined temperature so strongly and for so long that any micro-organisms and any of their spores contained on the surgical instruments are killed. In order to assure and inform a user, for example the staff who would like to use the sterile instruments in the operating room, that the instruments have indeed undergone a sterilization process and the use of said instruments on a patient is unproblematic with regards to a risk of infection, different embodiments of sterile displays for sterile containers have already been suggested in the prior art.

For example an exclusively manually actuatable sterile display in the form of a seal for a sterile container is known from DE 33 16 141 A1. The seal, which may only be accessed by a predetermined group of personnel, displays in its intact state attached to the sterile container that sterilized objects, in particular surgical instruments, are in the sterile container. It is disadvantageous in the case of this type of sterile display that the seal must be manually attached after the sterilization process, tested for integrity, and removed again before opening of the sterile container, or at least destroyed. The sterilization process must also be precisely monitored for a reliable evaluation of the sterility, due to the manual attaching of the seal.

Another type of sterile display is for example known from EP 0 412 571 B1. A sterile display for a sterile container is described therein, said sterile display including a display element for the display of a performed sterilization of the contents of the sterile container. For this purpose the display element comprises a spring made from a shape memory alloy, which makes available a spring load only upon exceeding a predetermined temperature, preferably the sterilization temperature. By means of the suddenly applied spring load, a locking member is transferred to a closed position in which it is visible that a sterilization has taken place. It is disadvantageous that for the sterile display a comparatively cost-intensive spring made from a shape memory alloy is used. It is further disadvantageous that such a spring cannot be brought as often as necessary into its stressed shape-memory position, but rather it is subject to restrictions with respect to its lifetime and thereby also with respect to the possible sterilization processes of the sterile container. Finally the sterile display of EP 0 412 571 B1 must be manually put back in its open position upon opening of the sterile container.

SUMMARY

On the other hand the invention is based on the object of improving the reliability of a sterile display for a sterile container, using structurally as simple as possible means. It is an object here that the sterile display has a high operational safety and a design which is as simple as possible. It is a further/another goal to ensure a comparatively high number of sterilization or treatment cycles.

This object is solved by means of a sterile display for a medical sterile container having a thermally actuatable display apparatus for the display of a first and a second sterility condition of the sterile container, wherein the display apparatus includes an adjustment mechanism having at least one spring-biasable/biased actuator element which can be transferred by means of external heating from a first stress state in which the first sterility condition can be displayed, to a second stress state in which the second sterility condition can be displayed, wherein the adjustment mechanism includes a thermo-bimetal element which in the unactuated design position retains the actuator element in its first stress state and releases, by means of its thermally conditional actuation, the actuator element of the adjustment mechanism which then, because of the spring bias, can be transferred from the first stress state to the second stress state.

A first independent aspect of the invention therefore provides that a sterile display or indicator for a medical sterile container comprises a thermally actuatable display apparatus for the display of a first and a second sterility condition of the sterile container. The display apparatus thereby comprises an adjustment mechanism having a spring element which can be transferred by means of external heating from a first stress state corresponding to the first sterility condition to be displayed, to a second stress state corresponding to the second sterility condition to be displayed. According to the invention, the adjustment mechanism comprises a thermo-bimetal element wherein by means of its heat dependent actuation the spring element of the adjustment mechanism can be transferred from the first stress state (loaded) to the second stress state (unloaded).

Through the use of a thermo-bimetal element as actuating means for the spring element there arises a comparatively constructively simple and thereby economically manufacturable construction of the sterile display. In particular the thermo-bimetal element is comparatively economically providable in comparison to the shape memory spring suggested in EP 0 412 571 B1 because a spring made from such a shape memory alloy clearly requires more effort to manufacture. In addition the sterile display according to the invention has a comparatively high lifetime with respect to the shape memory spring since the thermo-bimetal element permits a high number of sterilization cycles or treatment cycles. The term thermo-bimetal element is understood to mean a metal strip which is possibly also angled and which is made of two layers of different metals which are connected to each other by material fit or by positive (form-locking) fit. The invention makes use of the property that a temperature change which can be influenced by and thus definable by the material composition brings about a change of the shape in such a thermo-bimetal element. This manifests itself in this preferred case by a bending of the thermo-bimetal element, wherein the deflection direction can be defined by the material composition. In this way, the thermo-bimetal element can take two positions depending on temperature, of which the one represents a spring locking position and the other represents a spring release position.

In addition the first sterility condition to be displayed may be an unsterile state of the sterile container and the second sterility condition to be displayed may be a sterile state of the sterile container. Here a sterile state is defined as a state in which objects such as surgical instruments for example are rid of materials and objects of living micro-organisms including their dormant stages (e.g. spores). In order for a user of the sterile container, for example for the staff that performs the sterilization process, or for the staff in the operating room that monitors the state of the sterile container, to configure the display as simply and intuitively as possible, the unsterile state and the sterile state of the sterile container may each be indicated with an unambiguous marking. It has been shown to be particularly advantageous, i.e. unambiguously and intuitively recognizable, when the unsterile state is indicated by a red marking and the sterile state is indicated by a green marking. In addition or in alternative to the colored markings, the indication of the sterility conditions may also be performed by unambiguous symbols, such as for example a tick for the sterile state and a cross for the unsterile state, or similar such symbols. Ideally the display apparatus may be developed in its design such that in each state the marking corresponding to said state can be individually seen, so that the display in each case is unambiguous, that means unmistakable.

Preferably the first stress state is a loaded state and the second stress state is an essentially unloaded state of the actuator element (spring). The transfer of the actuator element (spring) of the adjustment mechanism from a loaded state to the essentially unloaded (more relaxed) state offers the advantage that the thermo-bimetal element releases an already stored (spring) force, such that a particularly reliable sterile display is ensured.

In a particularly advantageous embodiment of the invention, a display element of the display apparatus can be brought by means of the transferring of the actuator element (spring) in a translational movement, from a position displaying the first sterility condition to a position displaying the second sterility condition. In this way a particularly simple, reliable and durable construction of the sterile display is possible. For example the display element may be configured such that it shows or makes visible a first unique marking in the first position and a second unique marking in the second position.

It has proved to be advantageous when the actuator element of the adjustment mechanism comprises a spring element, preferably a (biasable) compression spring (helical spring) because in the case of the application according to the invention this ensures a long lifetime of the adjustment mechanism and thus of the entire sterile display. This is ensured in the case of a compression spring through its comparatively high mechanical long term stressability. The compression spring may be for example a helical compression spring which is distinguished by its comparatively low manufacturing costs and a simple system integration due to its constructive design. Compression springs are in addition available in many standard designs and are therefore economical.

Another optionally independent or additional aspect of the invention provides that the thermo-bimetal element, upon reaching and/or exceeding a definable (fixable) sterilization temperature, is actuatable or changes thereby its position or another property in order to cooperate with the actuator element. In particular the employed thermo-bimetal may be configured and/or selected in dependence on the sterilization temperature such that it actuates or releases the actuator element upon the exact reaching and/or exceeding of a definable temperature.

According to another optionally independent or additional aspect of the invention, the thermo-bimetal element may be configured as an essentially flat, optionally also angled, strip which upon reaching and/or exceeding the sterilization temperature deflects from a retaining position retaining the actuator element to a release position transferring (releasing or freeing) the actuator element. This configuration of the invention permits a particularly simple and compact construction of the sterile display since the thermo-bimetal element configured as a flat (optionally angled) strip requires only little space within the sterile display and/or the adjustment mechanism. In addition a deflection movement of a strip may be utilized in a constructively simple way, that means in a technically controlled way. In this way a reliable and safe retaining of the actuator element in its loaded state by means of the thermo-bimetal element is possible without any need to be concerned about an undesired release of the actuator element and thereby an undesired switching of the display apparatus.

Another optionally independent or additional aspect of the invention provides that the adjustment mechanism comprises a reset apparatus for the resetting of the display apparatus from the second sterilization state to be displayed to the first sterilization state to be displayed. Advantageously it can be ensured through this reset apparatus that a user or operator of the sterile container can bias or load the reset apparatus with his/her muscle strength such that a simple use of the sterile display or of the entire sterile container is permitted.

In a particularly advantageous embodiment variant of the invention, the reset apparatus is a spring element, preferably a compression spring. Thereby a comparatively simple, economical and reliable construction of the sterile display may be achieved. For a reliable resetting of the display apparatus, the spring force of the reset apparatus may be greater than the spring force of the actuator element. In other words the resetting force of the reset apparatus may be greater than the operating force of the actuator element.

According to another optionally independent or additional aspect of the invention, the reset apparatus of the adjustment mechanism may be biasable by manual closing or locking the sterile container in the resetting direction. That means that a user or operator of the sterile container biases the reset apparatus upon closing of the same, for example by attaching or placing a container lid which closes the sterile container, onto the sterile container and/or through the closing movement of the reset apparatus by means of the application of his/her muscle strength in the resetting direction. For this purpose an actuating mechanism may be provided which cooperates with the reset apparatus and the sterile container and/or the container lid such that the reset apparatus may be thus biased. For example a type of push-button may be provided as the actuating mechanism which is actuated upon placing of the container lid and/or by means of the closing movement of the container lid, and this actuating force is transmitted by a lever mechanism or similar at the reset apparatus such that the same is thus biased.

A further advantageous embodiment of the invention provides that the reset apparatus can be actuated by manual opening of the sterile container for the resetting of the display apparatus from the second sterilization state to be displayed to the first sterilization state to be displayed. That means that the display apparatus, upon opening of the sterile container, for example by opening of a container lid, is switched automatically by the reset apparatus, that means without further intervention of a user, from the display of the sterile state to the display of the unsterile state. In this way the operational safety of the sterile container as a whole is additionally increased since the resetting cannot be omitted or forgotten by a user of the sterile container.

In order to bias the actuator element for the next sterilization process, the actuator element of the adjustment apparatus according to another optionally independent or additional aspect of the invention may be biasable upon manual opening of the container lid by means of the unloading reset apparatus. That means that a part of the resetting force or resetting energy stored by the reset apparatus is used further for the resetting of the display apparatus in the "unsterile" direction and a further part of the resetting force or resetting energy is used for the biasing of the actuator element. With this configuration therefore, the user need only apply a force sufficient for the biasing of the reset apparatus when bringing the container lid onto the sterile container and/or when closing the same. After the sterilization process with closed container lid, that means after adjustment of the display apparatus to "sterile" has occurred and/or after reaching of the sterilization temperature and subsequent opening of the sterile container, the actuator element of the adjustment mechanism can thus be biased already for the next sterilization process. This embodiment of the invention therefore improves additionally the operational safety of the sterile container or the display apparatus since a biasing of the actuator element cannot be forgotten by a user.

Another optionally independent or additional aspect of the invention provides that the reset apparatus comprises a return element by which the display element of the display apparatus can be brought back in a translational movement from the position displaying the second sterility condition to the position displaying the first sterility condition. In this way a constructively particularly simple and compact construction of the sterile display is possible.

The reliability of the sterile display with respect to the transferring from a sterility condition to the other sterility condition and vice versa may be further improved when the actuator element is indirectly or directly biasable by the reset apparatus which is unloading due to the resetting movement. That means that the actuator element is biased with the resetting of the display apparatus from the one to the other sterility condition to be displayed by the resetting force (alone) of the reset apparatus, and is biased for the next application in the position in which it is held by the thermo-bimetal element.

For this purpose it may be advantageous when the resetting force of the reset apparatus is greater than the transferring force of the actuator element. This measure ensures that the actuator element is always biased for the next use of the sterile display.

According to another optionally independent or additional aspect of the invention, the display apparatus may be accommodated in a housing fixable to the sterile container. This causes the advantageous effect that the sterile display may be fixed to the sterile container in a single housing in a compact design.

For a particularly simple assembly of the sterile display the housing may be fixable to the sterile container by means of a snap connection. A comparatively costly screw connection is thus not necessary.

Another optionally independent or additional aspect of the invention provides that the sterile container comprises a carrier plate to which the housing that accommodates the display apparatus or, in place of the housing a dummy of the same, is optionally fixable. In this way a sterile container may be equipped or not equipped with a sterile display according to the invention, as desired. For example if due to a customer request no sterile display should be present on a sterile container, a yet more economical simplified dummy can be attached to the sterile container in place of the sterile display.

In order to achieve a particularly light sterile container with respect to its weight, the sterile container and/or the sterile container lid may be made from an appropriate plastic material, in particular from polyetheretherketone (PEEK) or polyphenylenosulfone (PPSU).

BRIEF DESCRIPTION OF THE DRAWING FIGURES

The invention is explained in closer detail below on the basis of preferred exemplary embodiments with reference to the accompanying drawings. In the drawings:

FIG. 1 shows a front perspective view of a sterile display according to the invention, FIG. 2 shows a rear perspective view of a partially sectioned sterile display according to the invention, FIG. 3 shows a front perspective view of a display element of a sterile display according to the invention, FIG. 4 shows another rear perspective view of a partially sectioned sterile display according to the invention, wherein by way of illustration an arranged thermo-bimetal element according to the invention is hidden, FIG. 5 shows a front perspective view of a sterile display according to the invention which is fixed to a medical sterile container, FIG. 6 shows a perspective view of a medical sterile container having a display dummy attached to it instead of a sterile display, and FIG. 7 shows a rear perspective view of a carrier plate of a medical sterile container, to which a sterile display according to the invention is fixed by means of a snap connection.

Identical or similar components are consistently provided with the same reference numerals.

DETAILED DESCRIPTION

FIG. 1 shows a perspective front view of an exemplary embodiment of a sterile display 1 according to the invention, which serves for the display of a sterility condition of a medical sterile container 2 shown in passing in FIGS. 5 and 6. In particular the sterile display 1 is in addition provided to show two different sterility conditions of the sterile container 2, that means either "sterile" or "not sterile", and optionally to automatically lock the sterile container 2 in the sterile state (when the sterile state is reached). As mentioned above, said sterile container serves for the accommodating of surgical instruments before, during and after a sterilization process.

The sterile display 1 is accommodated or received in an essentially cuboidal housing 4 which is made from a plastic material suited for the medical purpose. It is easy to recognize that the display of the two different sterility conditions takes place optically by means of a display apparatus 6. For this purpose the display apparatus 6 comprises a display element 8 which comprises on a front side 10 two circular markings 12, 14 which display the respective sterility condition of the sterile container 2 preferably in intuitively interpretable and clearly perceptible colors—the color red for the first (nonsterile) sterility condition and the color green for the second (sterile) sterility condition. Thereby the display element 8 of the display apparatus 6 acts together with a recess 16 of the housing 4, which recess 16 is suited or sized such that in each one of the two possible sterility conditions only exactly one of the two circular markings 12, 14 is exposed by the recess 16 and is thus externally visible. In FIG. 1 the display element 8 is located in a position or location in which only the circular marking 14 can be seen through the recess 16.

In FIG. 2 which shows a perspective front view of the display element 8 of the display apparatus 6, both markings 12, 14 which are arranged on the front side 10 of the display element 8 are easy to recognize. It is equally visible that the display element 8 is configured as an essentially cuboidal slider or piston. The display element 8 is preferably made from a plastic material suited for the medical purpose.

FIG. 3 shows a rear perspective view of the sterile display 1 partially sectioned or exposed for illustration purposes. It is easy to recognize that the bar-shaped housing 4 of the sterile display 1 comprises several internally lying longitudinal sections/areas which are partially separated from each other through molded bars comprised in the housing. For illustration purposes a rear-sided housing part/housing rear wall of the housing 4 is hidden in FIG. 3 in order to show the inner construction of the sterile display 1, in particular that of the display apparatus 6. Accordingly the housing 4 of the sterile display 1 in the ready-to-use condition is closed, preferably closed all-around.

In the housing 4 of the sterile display 1 the display apparatus 6 according to FIG. 3 is arranged in a left-side housing end-section, wherein by means of its piston-like display element 8, from which only a reverse side 18 can be seen in FIG. 2, both of the different sterility conditions of the sterile container 2 can be optically shown. For a display which is convertible or switchable from one sterility condition to the other sterility condition of the sterile container 2, the display element 8 is longitudinally displaceably arranged in the left-side display section 20 of the housing 4 and supports itself on the left (in FIG. 3) end face of the housing 4 against a support spring 22 which in this exemplary embodiment is a compression spring. By a translational movement, i.e. displacing, of the display element 8 in the longitudinal direction of the housing 4, it is possible for two different sterility conditions of the sterile container 2 to be displayed to a user or operator of the sterile container 2, who for example can be a member of staff in the operating room of a clinic. As described above, the longitudinal displacement of the display element 8 causes either the one marking 12 or the other marking 14 to be exposed by the recess 16 on the housing top side and/or housing front side and thus is visible to the outside.

Furthermore an adjustment mechanism 24 of the display apparatus 6 is arranged in the housing 4 for the actuation of the display element 8 into the two positions for displaying different sterility conditions. The adjustment mechanism 24 includes an actuator element 26 for transferring of the display element 8 from a first position/location in which the marking 12 corresponding to a first sterility condition is exposed by the recess 16, to a second position/location in which the marking 14 corresponding to a second sterility condition is exposed by the recess 16. That means that the display element 8 can be displaced by means of an actuation by the actuator element 26 from the position shown in FIGS. 1 and 3 by a translational movement to the left (in FIG. 3) in the direction against the support spring 22. For this purpose the actuator element 26 comprises a longitudinally extending cylindrically shaped actuator tappet 28 which can be brought/lies on its end side in contact with the display element 8.

The actuator element 26 extends in the housing 4 in the longitudinal direction (to the right in FIG. 3) away from the display element 8 and further comprises a clamping plate 30 and a spring section 32. Around the spring section 32 extends a spring element 34 which in this exemplary embodiment is a compression spring in the form of a coil spring. In order to achieve a biasing of the actuator element 26 in the adjustment direction of the display element 8, the spring element 34 is arranged between two spring shoulders in the form of a first bar (shoulder) 36 of the actuator tappet 28 and a second bar 38 of the housing 4, against which the spring element 34 supports itself. A cylindrical section 40 of the actuator element 26 (right end-section of the actuator tappet 28) extends in the longitudinal direction of the housing 4 through the second bar 38, in order to optionally come into contact with a third bar 41 of the housing 4, which bar 41 serves as a travel stop for the actuator element 26.

In FIG. 4, which shows another perspective rear view of the sterile display 1 which is partially sectioned or exposed for illustration purposes, it is easy to recognize that the actuator element 26 cooperates with a thermo-bimetal element 44 in the form of an angled metal strip. Contrary to the illustration in FIG. 3 in which the thermo-bimetal element 44 is hidden in order to be able to completely show the actuator element 26, the thermo-bimetal element 44 is now shown also in FIG. 4.

The thermo-bimetal element 44 is made in the form of a bimetallic strip or tongue of two layers of different metals. It can also be recognized that the thermo-bimetal element 44 is fixed at a first longitudinal end-section by means of the clamping plate 30 through a screw connection at the actuator element 26 (actuator tappet 28). As shown in FIG. 4, the thermo-bimetal element 44 is located on its second longitudinal end-section in a positive (form-locking), yet releasable as needed, connection with a retaining element 46 of the housing 4. The retaining element 46 is presently configured as a spigot or pin, preferably at the third housing bar 41, which can engage in a cross-hole at the thermo-bimetal element 44 (bimetallic strip). In order to retain the actuator element 26 by means of the thermo-bimetal element 44 in a holding position of the same and optionally to retain it in a position biased by the spring element 34, and optionally to release it by means of the thermo-bimetal element 44 into a release position of the same in the displacement direction of the display element 8, the metal layers of the thermo-bimetal element 44 are arranged such that the thermo-bimetal element 44 deflects or bends upon reaching and/or exceeding a definable temperature such that in this release position it is out of contact with the retaining element 46 of the housing 4. In this way the display element 8 can be pushed or displaced via the actuator tappet 28 in the longitudinal direction from the position shown in FIGS. 3 and 4 against the support spring 22 (to the left) through a deflection of the thermo-bimetal element 44 and the spring force of the spring element 34 thus released.

Further it can be seen in FIG. 4 that the adjustment mechanism 24 has a reset apparatus 48 acting in the longitudinal direction of the housing 4. The reset apparatus 48 is executed in the form of a cylinder rod 50 having a compression spring 52 surrounding the same, whereby in this exemplary embodiment it is a compression spring in the form of a coil spring. This is in principle assembled in opposition to the spring element 34, that means that while the spring element 34 pushes the actuator tappet 28 to the left according to FIG. 3, the compression spring 52 biases the cylinder rod 50 (in parallel to the actuator tappet 28) to the right. The reset apparatus 48 is therefore additionally provided to transfer or reset the display element 8 from the second position in which the marking 14 corresponding to a second sterility condition is exposed by the recess 16, back to the first position in which the marking 12 corresponding to a first sterility condition is exposed by the recess 16. In other words the display element 8 previously displaced by the actuator element 26 to "sterile." is displaced/pulled by means of the reset apparatus back to "unsterile".

In order to bias, together with the returning of the display element 8, also the spring element 34 of the actuator element 26 for its next use, whereby the spring energy of the spring element 34 is released by means of a deflection of the thermo-bimetal element 44, the compression spring 52 comprises a greater spring constant or spring force than the spring element 34 of the actuator element 26. By means of the front-sided pressing arrangement of the actuator tappet 28 on the piston shaped display element 8, the spring element 34 of the actuator element 26 can in this way be biased by means of the spring force of the compression spring 52 of the reset apparatus 48.

For this transferring (back) of the display element 10, the cylinder rod 50 of the reset apparatus 48 comprises at a first (left) longitudinal end 54 a return element (collar) 56 which can be brought into or is in (in FIGS. 3 and 4) a positive (form-locking) engagement (undercut) with a recess (slot) 58 of the display element 8. In order to retract the display element 8 in this way in the longitudinal direction of the housing 4 to the right (in FIGS. 3 and 4), the compression spring 52 of the reset apparatus 48 is arranged between two spring shoulders 60, 62 in the form of two bars of which the one bar 60 is configured at the housing 4 and the other bar 62 is configured at the cylinder rod 50. In order to bias the compression spring 52, the cylinder rod 50 is connected at a second, right longitudinal end 64 with a first end of a joint lever 66 by means of a hinge pin 68. In FIG. 4 it is easy to recognize that the joint lever 66 is connected at its other end by means of a hinge pin 70 to a control cam 72 of the adjustment mechanism 24. The control cam 72 is configured as an essentially cuboidal bolt (from plastic) which is guided from the housing 4 in a transverse direction with respect to the movement of the actuator element 26 or the reset apparatus 48, and protrudes longitudinally displaceably from the housing 4. Further it can be seen in FIG. 4 that the control cam 72 cooperates with a resetting spring 74 which biases the control cam 72 in a direction away from the housing 4. In a position of the control cam 72, in which its resetting spring 74 is loaded, the control cam 72 can be retained in or on the housing 4 through an interaction with the housing 4. According to this configuration of the adjustment mechanism 24 an inserting movement of the control cam 72 is transmitted transversely to the housing longitudinal direction via the joint lever 66 to the cylinder rod 50 and this is displaced in the housing longitudinal direction (to the left) against the compression spring 52. In addition the collar 56 is spaced from the slot 58 in the display element 8 and permits this to be moved to the left upon exertion of a thrust load from the actuator tappet 28. At the same time it is possible to bias the compression spring 52 of the reset apparatus 48 by an actuation of the control cam 72 in the direction into the housing 4 for the above-described resetting of the display element 8.

FIG. 5 shows a front perspective view of the sterile display 1 according to the invention in a state fixed to the sterile container 2. It is easy to recognize that the sterile display is arranged for this purpose on a carrier plate 76 of the sterile container 2. In order to allow a modular use of the sterile container 2, that means to realize several products for the user with a single configuration of the actual sterile container 2, the carrier plate 76 can also receive a display dummy 78 instead of the sterile display 1.

Furthermore FIG. 6 shows, in a perspective view, a display dummy 78 corresponding to the carrier plate 76 of the sterile container 2, whose external form and/or size is suited to the sterile display 2 and which is attached instead of the sterile display 2 to the sterile container 2.

In FIG. 7 which shows a rear perspective view of the carrier plate 76 of the sterile container 2, it is easy to recognize that the sterile display 1 according to the invention is fixed to the carrier plate 76 by means of a snap connection 80. In this way the sterile display 1 can be easily engaged to the carrier plate and optionally also released again.

The operation or use of the sterile display 1 according to the invention may proceed as follows.

For the first-time use of the sterile display 1, the spring element 34 of the actuator element 26 must be manually biased one-time, in which the thermo-bimetal element (bimetallic strip) 44 is housed on its end side at the retaining element (spigot/pin) 46. Assuming that the spring element 34 of the actuator element 26 is already biased, upon closing of the sterile container 2 filled with surgical instruments, the compression spring 52 of the reset apparatus 48 is biased by means of an actuation of the control cam 72 in the direction into the housing 4 via the joint lever 66, said actuation being performed by the muscle power of a user, and a possibility of a displacement of the display element 8 to the left is permitted.

By means of a heating effect applied from outside of the sterile container 2, for example in an autoclave used for the sterilization process, the thermo-bimetal element 44 is deflected upon the reaching and/or exceeding of a defined sterilization temperature which for example is approximately 90° C., and thus brought out of contact with the retaining element 46 of the housing 4. In this release position the spring force or spring energy of the spring element 34 of the actuator element 26 is released such that the display element 8 of the display apparatus 6 is displaced (to the left) by the actuator tappet 28 for the display of the sterile state. Now it is optically displayed to the user of the sterile container 2 that the sterile container 2 is in a sterile state.

Upon opening the sterile container 2, for example in order to be able to remove the sterile surgical instruments, the control cam 72 is released so that also the reset apparatus 48 which is connected to the control cam 72 by means of the joint lever 66 is moved by the release of the spring energy of the compression spring 52, wherein said spring energy is stored upon closing of the sterile container 2. By means of the return element (collar) 56, on the one hand the display element 8 for the displaying of the sterile container 2 which is now in its unsterile state again is displaced back, and on the other hand the spring element 34 of the actuator element 26 is at the same time automatically biased for its next use.

Disclosed is a sterile display for a sterile container having a thermally actuatable display apparatus for the display of a first and a second sterility condition of the sterile container closed by means of a container lid. The display apparatus comprises an adjustment mechanism having an actuator element which can be transferred, when the container lid is closed and by means of external heating, from a first stress state in which the first sterility condition can be displayed, to a second stress state in which the second sterility condition can be displayed. According to the invention the adjustment mechanism comprises a thermo-bimetal element wherein, by means of its actuation, the actuator element of the adjustment mechanism can be transferred from the first stress state to the second stress state.

The invention claimed is:

1. A sterile display for a sterile container comprising:
a thermally actuatable display apparatus for the display of a first sterility condition and a second sterility condition of the sterile container, wherein the display apparatus comprises an adjustment mechanism having at least one spring-biasable actuator element which can be transferred by means of external heating from a first stress state in which the first sterility condition can be displayed, to a second stress state in which the second sterility condition can be displayed, wherein the adjustment mechanism comprises a thermo-bimetal element which in the unactuated design position retains the actuator element in the first stress state and releases the actuator element by means of a thermally conditional actuation, the actuator element of the adjustment mechanism which then, because of a spring bias, can be transferred from the first stress state to the second stress state.

2. A sterile display according to claim 1, wherein the first stress state is a loaded state and the second stress state is an unloaded state of the actuator element.

3. A sterile display according to claim 1, wherein a display element of the display apparatus can be brought, by means of the actuator element, into a translational movement from a position displaying the first sterility condition to a position displaying the second sterility condition.

4. A sterile display according to claim 1, wherein the actuator element comprises a compression spring which can be retained in a loaded position by the thermo-bimetal element.

5. A sterile display according to claim 1, wherein the thermo-bimetal element can be actuated with reaching or exceeding of a definable sterilization temperature.

6. A sterile display according to claim 5, wherein the thermo-bimetal element is configured as a flat or angled strip which deflects, upon reaching and/or exceeding the sterilization temperature, from one position retaining the actuator element to a position releasing the actuator element.

7. A sterile display according to claim 1, wherein the adjustment mechanism comprises a reset apparatus for an automatic resetting of the display apparatus from the second sterility condition to be displayed to the first sterility condition to be displayed.

8. A sterile display according to claim 7, wherein the reset apparatus comprises a compression spring which is configured acting opposingly to the compression spring of the actuator element in order to transfer upon release, owing to a biasing force, the display apparatus to a display position of the first sterility condition and at the same time to re-load the compression spring of the actuator element.

9. A sterile display according to claim 7, wherein the reset apparatus of the adjustment mechanism is biasable by means of manual closing of the sterile container in the resetting direction and is held in a biased position.

10. A sterile display according to claim 7, wherein the reset apparatus can be actuated by manual opening of the sterile container for resetting, by effect of spring force, the display apparatus from the second sterilization state to be displayed to the first sterilization state to be displayed.

11. A sterile display according to claim 7, wherein the reset apparatus comprises a compression spring and a return carrying element through which a display element of the display apparatus, upon release of the compression spring, can be brought back in a translational movement from the position displaying the second sterility condition to the position displaying the first sterility condition, and that releases an actuation of the display element by the actuator element upon loading of the compression spring.

12. A sterile display according to claim 7, wherein the actuator element is automatically biased by the unloading reset apparatus in the actuating direction of the actuator element.

13. A sterile display according to claim 12, wherein a resetting force of the reset apparatus is greater than a transferring force of the actuator element.

14. A sterile display according to claim 1, wherein the display apparatus is accommodated in a housing fixable to the sterile container.

15. A sterile display according to claim 14, wherein the housing is fixable to the sterile container by means of a snap connection.

* * * * *